(12) United States Patent
Swan et al.

(10) Patent No.: US 7,300,756 B2
(45) Date of Patent: *Nov. 27, 2007

(54) EPOXIDE POLYMER SURFACES

(75) Inventors: Dale G. Swan, St. Louis Park, MN (US); Melvin J. Swanson, Carver, MN (US)

(73) Assignee: SurModics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/844,667

(22) Filed: May 12, 2004

(65) Prior Publication Data

US 2004/0209305 A1 Oct. 21, 2004

Related U.S. Application Data

(63) Continuation of application No. 09/521,545, filed on Mar. 9, 2000, now Pat. No. 6,762,019, which is a continuation-in-part of application No. 09/227,913, filed on Jan. 8, 1999, now Pat. No. 6,465,178, which is a continuation-in-part of application No. 08/940,213, filed on Sep. 30, 1997, now Pat. No. 5,858,653.

(51) Int. Cl.
 *C12Q 1/68* (2006.01)
 *C12M 1/20* (2006.01)
 *C12M 1/34* (2006.01)
(52) U.S. Cl. .................. 435/6; 435/287.2; 435/287.9
(58) Field of Classification Search ............... 435/6, 435/287.2, 297.9
See application file for complete search history.

(56) References Cited

U.S. PATENT DOCUMENTS

| | | | |
|---|---|---|---|
| 4,056,208 A | 11/1977 | Prejean | |
| 4,332,694 A | 6/1982 | Kalal et al. | |
| 4,357,142 A | 11/1982 | Schall, Jr. et al. | |
| 4,363,634 A | 12/1982 | Schall, Jr. | |
| 4,542,102 A | 9/1985 | Dattagupta et al. | |
| 4,582,860 A | 4/1986 | Bigwood et al. | |
| 4,722,906 A | 2/1988 | Guire | |
| 4,973,493 A | 11/1990 | Guire | |
| 4,979,959 A | 12/1990 | Guire | |
| 4,994,373 A | 2/1991 | Stavrianopoulos et al. | |
| 5,002,582 A | 3/1991 | Guire et al. | |
| 5,217,492 A | 6/1993 | Guire et al. | |
| 5,414,075 A * | 5/1995 | Swan et al. ............ | 568/333 |
| 5,510,084 A | 4/1996 | Cros et al. | |
| 5,512,329 A | 4/1996 | Guire et al. | |
| 5,563,056 A | 10/1996 | Swan et al. | |
| 5,580,697 A | 12/1996 | Keana et al. | |
| 5,610,287 A | 3/1997 | Nikiforov et al. | |
| 5,637,460 A | 6/1997 | Swan et al. | |
| 5,641,658 A | 6/1997 | Adams et al. | |
| 5,643,580 A | 7/1997 | Subramaniam | |
| 5,654,162 A | 8/1997 | Guire et al. | |
| 5,707,818 A | 1/1998 | Chudzik et al. | |
| 5,714,360 A | 2/1998 | Swan et al. | |
| 5,718,726 A | 2/1998 | Amon et al. | |
| 5,741,551 A | 4/1998 | Guire et al. | |
| 5,744,515 A | 4/1998 | Clapper | |
| 5,783,502 A | 7/1998 | Swanson | |
| 5,858,653 A | 1/1999 | Duran et al. | |
| 5,919,626 A | 7/1999 | Shi et al. | |
| 5,942,555 A | 8/1999 | Swanson et al. | |
| 6,033,784 A | 3/2000 | Jacobsen et al. | |
| 6,057,100 A | 5/2000 | Heyneker | |
| 6,239,273 B1 | 5/2001 | Pease et al. | |

(Continued)

FOREIGN PATENT DOCUMENTS

| | | |
|---|---|---|
| WO | WO 91/16425 | 10/1991 |
| WO | WO 97/16544 | 5/1997 |
| WO | WO9958716 A1 | 11/1999 |

OTHER PUBLICATIONS

Chevrier, D. et al., "Rapid Detection of *Salmonella* Subspecies I by PCR Combined with Non-radioactive Hybridisation Using Covalently Immobilised Oligonucleotide on a Microplate", *FEMS Immunology and Medical Microbiology*, vol. 10, No. 3-4, pp. 245-251 (Feb. 1995).

Collioud, A. et al., "Oriented and Covalent Immobilization of Target Molecules to Solid Supports: Synthesis and Application of a Light-Activatable and Thiol-Reactive Cross-Linking Reagent", *Bioconjugate Chem.*, vol. 4, No. 6, pp. 528-536 (Nov./Dec. 1993).

Kanazawa, A. et al., "Polymeric Phosphonium Salts as a Novel Class of Cationic Biocides. VII. Synthesis and Antibacterial Activity of Polymeric Phosphonium Salts and Their Model Compounds Containing Long Alkyl Chains", *Jrnl. of Applied Polymer Science*, vol. 53, No. 9, pp. 1237-1244 (Aug. 29, 1994).

Nagasawa, J. et al., "Immobilization of DNA via Covalent Linkage for Use as Immunosorbent". *Jrnl. of Applied Biochem.*, vol. 7, pp. 296-302 (1985).

Nagasawa, J. et al., "Immunosorbent Consisting of DNA Immobilized on Oxirane-Activated Sepharose", *Jrnl. of Applied Biochem.*, vol. 7, pp. 430-437 (1985).

O'Donnell-Maloney, M. et al., "The Development of Microfabricated Arrays for DNA Sequencing and Analysis", *TIBTECH*, vol. 14, pp. 401-407 (Oct. 1996).

"Reacti-Bind™ DNA Coating Solution", *PIERCE*, 1 pg. (© Pierce Chemical Company—Jan. 1997).

"NucleoLink™ versus CovaLink™ Surfaces", *Nunc InterMed TechNote—Molecular Biology*, Oct. 1995, vol. 3, No. 17, 2 pgs.

*Primary Examiner*—Mark L. Shibuya
(74) *Attorney, Agent, or Firm*—Merchant & Gould P.C.

(57) ABSTRACT

Method and reagent composition for covalent attachment of target molecules, such as nucleic acids, onto the surface of a substrate. The reagent composition includes epoxide groups capable of covalently binding to the target molecule. Optionally, the composition can contain photoreactive groups for use in attaching the reagent composition to the surface. The reagent composition can be used to provide activated

6 Claims, No Drawings

U.S. PATENT DOCUMENTS

| | | |
|---|---|---|
| 6,309,822 B1 * | 10/2001 | Fodor et al. .................. 435/6 |
| 6,391,937 B1 | 5/2002 | Beuhler et al. |
| 6,465,178 B2 | 10/2002 | Chappa et al. |
| 6,476,215 B1 | 11/2002 | Okamoto et al. |
| 6,746,842 B2 | 6/2004 | Park et al. |
| 6,762,019 B2 | 7/2004 | Swan et al. |
| 2002/0146715 A1 | 10/2002 | Okamoto et al. |
| 2004/0241753 A1 | 12/2004 | Meier et al. |

* cited by examiner

EPOXIDE POLYMER SURFACES

Cross Reference To Related Applications

This application is a continuation application of application Ser. No. 09/521,545 filed on Mar. 9, 2000 now U.S. Pat. No. 6,762,019, which is a continuation-in-part of application Ser. No. 09/227,913 filed on Jan. 8, 1999, now U.S. Pat. No. 6,465,178, which is a continuation-in-part of application Ser. No. 08/940,213 filed on September 30, 1997, now U.S. Pat. No. 5,858,653, which application(s) are incorporated herein by reference.

TECHNICAL FIELD

The present invention relates to reagents and support surfaces for immobilization of biomolecules, such as nucleic acids and proteins.

BACKGROUND OF THE INVENTION

The immobilization of deoxyribonucleic acid (DNA) onto support surfaces has become an important aspect in the development of DNA-based assay systems, including the development of microfabricated arrays for DNA analysis. See, for instance, "The Development of Microfabricated Arrays of DNA Sequencing and Analysis", O'Donnell-Maloney et al., *TIBTECH* 14:401-407 (1996). Generally, such procedures are carried out on the surface of microwell plates, tubes, beads, microscope slides, silicon wafers or membranes.

A commonly used method for immobilizing cDNA's or PCR products into arrays is to first coat glass slides with polylysine, then apply the DNA and illuminate with UV light to photocrosslink the DNA onto the polylysine (for example, see Schena M, Shalon D, Heller R, Chai A, Brown P O, Davis R W, "Parallel Human Genome Analysis: Microarray-based Expression Monitoring of 1000 Genes", *Proc. Natl. Acad. Sci. USA* 93(20):10614-9 (1996)). One disadvantage of this approach is that the UV crosslinking causes undesirable damage to the DNA that is not all useful for the immobilization. Another disadvantages of this approach is that UV crosslinking tends to be limited to longer nucleic acids (e.g., over about 100-mers), as provided by cDNA's and PCR products (and in contrast to the shorter nucleic acids typically formed by synthesis and referred to as "oligonucleotides"). It appears that the potential damage induced by UV radiation (e.g., the formation of thymine dimers) is simply too great, and/or the extent of immobilization is insufficient, to permit shorter nucleic acids to be used. A population of longer nucleic acids, however, even when crosslinked by UV, will typically provide ample undamaged regions sufficient to permit accurate hybridization.

Only relatively few approaches to immobilizing DNA, to date, have found their way into commercial products. One such product for immobilizing oligonucleotides onto microwell plates is known as ["NucleoLink®"] NUCLEOL™, and is available from Nalge Nunc International (see, e.g., Nunc Tech Note Vol. 3, No. 17). In this product, the DNA is reacted with a carbodiimide to activate 5'-phosphate groups, which then react with functional groups on the surface. Disadvantages of this approach are that it requires the extra step of adding the carbodiimide reagent as well as a five hour reaction time for immobilization of DNA, and it is limited to a single type of substrate material.

As another example, Pierce has introduced a proprietary DNA immobilization product known as ["Reacti-Bind™"] REACTI-BIND™ DNA Coating Solutions" (see "Instructions REACTI-BIND™ DNA Coating Solution" January, 1997). This product is a solution that is mixed with DNA and applied to surfaces such as polystyrene or polypropylene. After overnight incubation, the solution is removed, the surface washed with buffer and dried, after which it is ready for hybridization. Although the product literature describes it as being useful for all common plastic surfaces used in the laboratory, it does have some limitations. For example, Applicants were not able to demonstrate useful immobilization of DNA onto polypropylene using the manufacturer's instructions. Furthermore, this product requires large amounts of DNA. The instructions indicate that the DNA should be used at a concentration between 0.5 and 5 µg/ml.

Corning sells a product called "DNA-BIND™" for use in attaching DNA to the surface of a well in a microwell plate (see, e.g., the DNA-BIND™ "Application Guide"). The surface of the DNA-BIND™ plate is coated with an uncharged, nonpolymeric, low molecular weight, heterobifunctional reagent containing an N-oxysuccinimide (NOS) reactive group. This group reacts with nucleophiles such as primary amines. The heterobifunctional coating reagent also contains a photochemical group and spacer arm which covalently links the reactive group to the surface of the polystyrene plate. Thereafter, amine-modified DNA can be covalently coupled to the NOS surface. The DNA is modified by adding a primary amine either during the synthesis process to the nascent oligomer or enzymatically to the preformed sequence. Since the DNA-BIND™ product is polystyrene based, it is of limited use for those applications that require elevated temperatures such as thermal cycling. Corning also sells an aminosilane-coated glass slide, under the tradename CMT-GAPS™ coated slides, which uses the same protocol as polylysine-coated slides for immobilizing DNA into microarrays.

TeleChem International, Inc. sells slides coated with an aldehyde silane as well as an aminosilane-coated slide. The aldehyde silane slides have very high backgrounds when fluorescence is used for detection. They also require an additional reduction step for stable immobilization.

Finally, SurModics, Inc., the assignee of the present invention, has recently introduced a coated glass slide, under the tradename 3D-Link™ that consists of a hydrophilic polymer containing amine-reactive ester groups immobilized onto the surface. For best results, this product also requires amine modification of the DNA to be immobilized. As expected, however, the reactive ester groups tend to be hydrolytically unstable, which limits the amount of time arrays can be printed without some loss of performance to approximately eight hours.

The role of epoxide groups, in the course of binding or immobilizing nucleic acids, has been described in various ways as well. For instance, Shi et al., U.S. Pat. No. 5,919,626 describe the attachment of unmodified nucleic acids to silanized solid phase surfaces. The method involves the use of conventional nonpolymeric reagents such as mercaptosilanes and epoxy-silanes which bond to the surface by forming siloxane bonds with OH groups on the glass surface.

See also, U.S. Pat. No. 5,925,552 (Keogh, et al., "Method for Attachment of Biomolecules to Medical Devices Surfaces"), which provides a method for forming a coating of an immobilized biomolecule on a surface of a medical device to impart improved biocompatibility for contacting tissue and bodily fluids. One such method includes converting a biomolecule comprising an unsubstituted amide moiety into an amine-functional material, combining the amine-functional material with a medical device biomaterial surface comprising a chemical moiety (such as, for example, an aldehyde moiety, an epoxide moiety, an isocyanate moiety, a phosphate moiety, a sulphate moiety or a carboxylate moiety) which is capable of forming a chemical bond with the amine-functional material, to bond the two materials together to form an immobilized biomolecule on a medical device biomaterial surface. Included within the long list of biomolecules described as being useful in this patent were "a DNA segment, a RNA segment, a nucleic acid" and others.

Also on the subject of epoxides, Nagasawa et al., (*J. Appl. Biochem.* 7:430-437, 1985) describe the use of Sepharoses activated with epichlorohydrin or bisoxirane (both of which provide epoxide groups) for immobilizing DNA as immunosorbents for DNA antibodies. See also, Wheatley, et al., *J. Chromatog. A* 726:77-90 (1996) and Potuzak, et al., *Nucl. Acids Res.* 5:297-303 (1978).

To date, however, there appears to be no description in the art, let alone commercial products, that provide an optimal combination of such properties as hydrolytic stability, ease of use, minimized DNA damage (due to exposure to crosslinking radiation), and the ability to immobilize underivatized nucleic acids and/or shorter nucleic acid segments. In turn, there appear to be no products presently available, nor descriptions in the art, that provide or suggest the ability to use polymer-pendent epoxide groups adapted to immobilize either short or long nucleic acids, let alone in both derivatized and underivatized forms, and suitable for immobilization onto surfaces.

Finally, Surmodics, Inc., the assignee of the present invention, has previously described a variety of applications for the use of photochemistry, and in particular, photoreactive groups, e.g., for attaching polymers and other molecules to support surfaces. See, for instance, U.S. Pat. Nos. 4,722,906, 4,979,959, 5,217,492, 5,512,329, 5,563,056, 5,637,460, 5,714,360, 5,741,551, 5,744,515, 5,783,502, 5,858,653, and 5,942,555.

SUMMARY OF THE INVENTION

The present invention provides a method and epoxide-based reagent composition for covalent attachment of target molecules onto the surface of a substrate, such as microscope slides, microwell plates, tubes, silicon wafers, beads or membranes. In a preferred embodiment, the method and composition are used to immobilize nucleic acid probes onto microscope slides, e.g., for use in printing DNA microarrays. The method and reagent of the present invention can be used to covalently immobilize either derivatized (e.g., amine-derivatized) or underivatized (i.e., not having a group added for the purpose of thermochemical reaction with an epoxide group) nucleic acids, and are particularly useful for underivatized nucleic acids. The immobilization method of this invention is very convenient to perform. In a preferred embodiment, the method involves the steps of coating a support with the reagent of this invention, printing the nucleic acid array, incubating the slide in a humid environment, blocking excess epoxide groups and washing the slide, after which it is ready for a hybridization assay.

Parent application U.S. Ser. No. 09/227,913, describes, inter alia, a comprehensive method and reagent composition for covalent attachment of target molecules onto the surface of a substrate, using a reagent that contains one or more thermochemically reactive groups (i.e., groups having a reaction rate dependent on temperature). Suitable groups are selected from the group consisting of activated esters such as N-oxysuccinimide ("NOS"), epoxide, azlactone, activated hydroxyl and maleimide groups.

The present application is particularly concerned with reagents having epoxide groups, in the manner described above, and provides further examples and advantages concerning the use of such epoxide-based reagents. Such advantages include, for instance, the ability to use the reagents to attach underivatized DNA, in addition to DNA derivatized to contain amine or other reactive groups, as described in parent application U.S. Ser. No. 09/227,913. Such advantages also include improved resistance to hydrolysis demonstrated by epoxides, as compared for instance, to NOS groups.

The present invention provides a method for immobilizing biomolecules, such as biopolymers selected from nucleic acids, proteins, and polysaccharides, the method comprising the steps of:

a) providing a solid support having a surface, b) providing a reagent comprising one or more epoxide groups, and optionally also comprising one or more photogroups, c) coating the reagent on the support surface (e.g., covalently attaching the polymeric reagent to the support surface by activation of the photogroups), d) providing a biopolymer having a corresponding thermochemical reactive group, e) attaching the biopolymer to the support by reacting its corresponding reactive group with the bound epoxide group, f) optionally blocking the remaining epoxide groups (e.g., using an amine reagent), and g) using the resultant coated support surface for its intended purpose, e.g., for the immobilization of biomolecules such as nucleic acids.

Applicants have found that polymers (and particularly hydrophilic polymers) containing epoxide groups, of the type described herein, have several advantages for DNA immobilization over previously used methods. These polymers, when coated onto silane-modified glass slides, for instance, provide an improved method for immobilizing underivatized DNA. Therefore, using these reagents, it is not necessary to modify the DNA with amines or other functional groups. Furthermore, the epoxide groups are significantly more stable to hydrolysis than are the amine-reactive ester groups. Compared with UV crosslinking of DNA onto polylysine or aminosilane, the coated surfaces of this invention are more convenient to use and tend to result in fewer undesirable side reactions, thereby resulting in less modification of the DNA.

A reagent composition of the invention preferably provides one or more epoxide (also known as "oxirane") groups pendent on a polymeric backbone, such as a hydrophilic polyacrylamide backbone. Optionally, and preferably, the reagent composition can also provide one or more pendent photoreactive groups. The photoreactive groups (alternatively referred to herein as "photogroups") can be used, for instance, to attach reagent molecules to the surface of the support upon the application of a suitable energy source such as light. The epoxide groups, in turn, can be used to form covalent bonds with appropriate functional groups on the target molecule.

Optionally, the composition and method of this invention can be provided in the manner described in parent application U.S. Ser. No. 08/940,213. In such an embodiment, the reagent composition can be used for attaching a target molecule to the surface of a substrate, and comprises one or more groups for attracting the target molecule to the reagent, and one or more epoxide groups for forming covalent bonds with corresponding functional groups on the attracted target molecule. Optionally, such a composition further provides photogroups for use in attaching the composition to a surface. In one embodiment, for instance, a plurality of photogroups and a plurality of ionic groups (e.g., cationic groups) are attached to a hydrophilic polymer backbone. This polymer can then be coimmobilized with a second polymer backbone that provides the above-described epoxide groups for immobilization of target molecules. Suitable ionic groups include quaternary ammonium salts, protonated tertiary amines and other cationic groups such as phosphonium compounds. Also included are tertiary amine groups capable of being protonated when placed in an acid environment. Quaternary ammonium salts include alkyl quaternary ammonium compounds, such as [3-(methacryloylamino)propyl]trimethylammonium chloride (MAPTAC), as well as aromatic quaternary ammonium groups such as pyridinium compounds. Phosphonium compounds include polymers prepared from monomers such as tributyl (4-vinylbenzyl)phosphonium chloride, and are described in *J. Appl. Polymer Sci.* 53:1237 (1994), the disclosure of which is also incorporated by reference.

The invention further provides a method of attaching a target molecule, such as a DNA molecule, to a surface, by employing a reagent as described herein. In turn, the invention provides a surface having target molecules such as nucleic acids attached thereto by means of such a reagent, as well as a material (e.g., microscope slide) that provides such a surface.

Generally, the reagent molecules will first be attached to the surface by activation of the photogroups, thereafter the target molecule, (e.g., a nucleic acid) is contacted with the bound reagent under conditions suitable to permit it to come into binding proximity with the bound polymer. The target molecule is thermochemically coupled to the bound reagent by reaction between the reactive groups of the bound reagent and appropriate functional groups on the target molecule.

The invention further provides a method of attaching a target molecule, such as a nucleic acid, to a surface, by employing a reagent as described herein. As used herein, with regard to describing the present invention, the word "oligonucleotide" (or "oligo") shall refer to a synthetic nucleic acid (as opposed to enzymaticaly prepared), and one that is typically shorter (e.g., on the order of 100-mer or less) than cDNA or PCR products formed enzymatically. The term "nucleic acid", in turn, will refer to all such products collectively.

The invention further provides a surface having nucleic acids attached thereto by means of such a reagent, as well as a material (e.g., a slide or microwell plate) that provides such a surface. In yet another aspect, the invention provides a composition comprising a reagent of this invention in combination with a target molecule that contains one or more functional groups reactive with the thermochemically reactive group of the reagent.

DETAILED DESCRIPTION

A preferred reagent composition of the present invention comprises a hydrophilic polymer bearing one or more pendent epoxide groups adapted to form a covalent bond with corresponding reactive groups of a target molecule, and also bearing one or more pendent photoreactive groups adapted to be used for attaching the reagent to a surface, either before, during and/or after reaction between the reagent and the target molecules. Optionally, a composition can include other components, in addition to the reagent polymer component, such as polymers having pendent ionic groups, and the like.

In another embodiment of the invention, it is possible to immobilize the reagent composition, and in turn the target molecules, without the use of the photoreactive group. For instance, the surface of the material to be coated can be provided with thermochemically reactive groups, which can be used to immobilize hydrophilic polymers having epoxide groups as described above. For example, a surface may be treated with an ammonia plasma to introduce a limited number of reactive amines on the surface of the material. If this surface is then treated with a hydrophilic polymer having epoxide groups, then the polymer can be immobilized through reaction of the epoxide groups with amines on the surface. Preferably, the concentration of epoxide groups on the polymer is in sufficient excess, relative to the concentration of amines on the surface to insure that a sufficient number of reactive groups remain following the immobilization to allow coupling with the nucleic acid sequence.

A polymeric backbone can be either synthetic or naturally occurring, and is preferably a synthetic copolymer of the epoxide monomer and diluent or other monomers resulting from addition or condensation polymerization. Naturally occurring polymers, such as polysaccharides or polypeptides can be used as well. Preferred diluent monomers are biologically inert, in that they do not provide a biological function that is inconsistent with, or detrimental to, their use in the manner described.

Suitable diluent monomers for use in preparing a reagent of this invention include acrylics such as hydroxyethyl acrylate, hydroxyethyl methacrylate, glyceryl acrylate, glyceryl methacrylate; acrylamide derivatives, such as acrylamide, methacrylamide, and acryloyl morpholine. Other synthetic polymers can be synthesized to include pendent epoxide groups in the manner described herein, including vinyls such as polyvinyl pyrrolidone and polyvinyl alcohol; nylons such as polycaprolactam, polylauryl lactam, polyhexamethylene adipamide and polyhexamethylene dodecanediamide; polyurethanes and polyethylene oxide, as well as combinations and copolymers thereof.

A reagent of the present invention preferably includes a hydrophilic polymer bearing a desired average number of photogroups and epoxide groups per average unit length or molecular weight, the combination dependent upon the reagent selected. The epoxide monomer can also be selected to provide any desirectivity. The diluent comonomers are preferably hydrophilic (e.g., water soluble), with acrylamide and vinylpyrrolidone being particularly preferred.

Epoxide-containing polymers of the present invention can be prepared from monomers, such as glycidyl acrylate, glycidyl methacrylate, allylglycidyl ether, and glycidyl vinyl ether. Useful monomers are available from a variety of sources, for instance glycidyl acrylate (Pfaltz & Bauer Chemicals, cat. # G03480), glycidyl methacrylate (Aldrich cat # 15,123-8), allylglycidyl ether (Aldrich, cat # A3,260-8), glycidyl vinyl ether (Aldrich, cat. # 45,865-1), and glycidyl vinylbenzyl ether (Aldrich cat. # 45,867-8).

Epoxide monomers can also be made, such as by reaction of 2-isocyanatoethylmethacrylate with glycidol. Epoxide polymers can also be prepared by reacting hydroxyl polymers (e.g., polyhydroxypropylacrylamide) with epichlorohydrin. Other epoxide monomers and polymers can be made by those skilled in the art having spacers of various lengths and with various polarities. Other examples of suitable monomers are described in U.S. Pat. No. 5,763,629.

Epoxide-containing polymers can also be synthesized by reacting hydroxyl- or amine-containing polymers with diepoxides. Currently, an epoxide activated-Sepharose is available (Sigma) that is made by reacting Sepharose gel beads with 1,4-butanedioldiglycidyl ether. This, or other diepoxides, (e.g., ethylene glycol diglycidyl ether, diepoxyoctane or diepoxydecane) can be used for derivatizing either amine or hydroxyl polymers to make polyepoxides. For example, polyhydroxypropylacrylamide or a copolymer containing a photomonomer can be reacted with an excess of 1,4-butanedioldiglycidyl ether to make a polyepoxide that can then be immobilized onto a surface.

Useful epoxide monomers include those of the general formula:

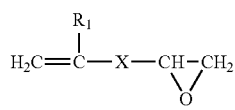

Where $R_1$ is either $CH_3$ or H and X is a noninterfering radical, preferably selected from the group:

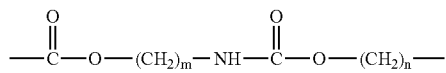

where m=2-6 and n=1-10;

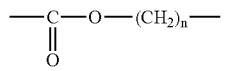

where n=1-10;

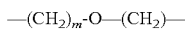

where m=0 or 1, and;

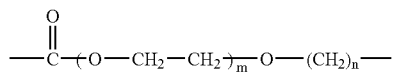

where m=1-20 and n=1-10.

Without intending to be bound by theory, it would appear that epoxide groups can be used to immobilize underivatized DNA in a covalent fashion, and presumably due to a mechanism of reacting with amine groups on the purine and pyrimidine rings, such as cytosine and adenine, or with terminal hydroxyl groups.

Reagents of the invention optionally carry one or more pendent latent reactive (preferably photoreactive) groups covalently bonded to the polymer backbone. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency. Hence, photoreactive aryl ketones are particularly preferred.

The azides constitute a preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene. Photoactivatible aryl ketones such as benzophenone and acetophenone are of particular importance inasmuch as these groups are subject to multiple reactivation in water and hence provide increased coating efficiency.

Upon activation of the photoreactive groups, the reagent molecules are covalently bound to each other and/or to the material surface by covalent bonds through residues of the photoreactive groups. Exemplary photoreactive groups, and their residues upon activation, are shown as follows.

| Photoreactive Group | | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—SO$_2$—NH—R' |
| phosphoryl azides | phosphoramide | (RO)$_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Copolymers can be prepared using epoxide-containing monomers as described above, using techniques known to those skilled in the art. Preferably, the epoxide monomers and comonomers undergo free radical polymerization of vinyl groups using azo initiators such as 2,2'-azobisisobutyronitrile (AIBN) or peroxides such as benzoyl peroxide. The comonomers selected for the polymerization are chosen based on the nature of the final polymer product. For example, a photoreactive polymer containing epoxide groups can be prepared by the use of a monomer mixture that includes one or more monomers containing a photoreactive group and one or more second monomers containing an epoxide group.

An epoxide-functionalized polymeric reagent of this invention can be prepared by appropriate derivatization of a preformed polymer or, more preferably, by polymerization of a set of comonomers to give the desired substitution pattern. The latter approach is preferred because of the ease of changing the ratio of the various comonomers and by the ability to control the level of incorporation into the polymer.

The composition of the final polymer can be controlled by mole ratio of the monomers charged to the polymerization reaction. Typically the epoxide monomers are used at relatively low mole percentages of the total monomer content of the polymerization reaction, with the remainder of the composition consisting of a relatively low mole percent of photomonomers, and the remainder of monomers which are neither photoreactive nor thermochemically reactive toward the nucleic acid sequence. Examples of such monomers include, but are not limited to, acrylamide, acrylic acid and N-vinylpyrrolidone. Based on the relative reactivities of the monomers used, the distribution of the monomers along the backbone is largely random.

In a preferred embodiment, for instance, a reagent composition is formed having between about 5 mole % and about 25 mole % epoxide monomer (more preferably between about 10 mole % and about 20 mole %); between about 0.1 mole % and about 5 mole % photomonomer (more preferably between about 0.5 mole % and about 2 mole %), and the remainder (to 100 mole %) other monomers.

The present invention provides a method and reagent composition for covalent attachment of target molecules onto the surface of a substrate, such as slides formed of organosilane-pretreated glass, organosilane-pretreated silicon, silicon hydride, or plastic. In one embodiment, the method and composition are used to immobilize nucleic acid probes onto plastic materials such as microwell plates, e.g., for use in hybridization assays. In a preferred embodiment the method and composition are adapted for use with substantially flat or molded surfaces, such as those provided by organosilane-pretreated glass, organosilane-pretreated silicon, silicon hydride, or plastic (e.g., polymethylmethacrylate, polystyrene, polycarbonate, polyethylene, or polypropylene). The reagent composition can then be used to covalently attach a target molecule such as a biomolecule (e.g., a nucleic acid) which in turn can be used for specific binding reactions (e.g., to hybridize a nucleic acid to its complementary strand).

Support surfaces can be prepared from a variety of materials, including but not limited to plastic materials selected from the group consisting of crystalline thermoplastics (e.g., high and low density polyethylenes, polypropylenes, acetal resins, nylons and thermoplastic polyesters) and amorphous thermoplastics (e.g., polycarbonates and poly(methyl methacrylates). Suitable plastic or glass materials provide a desired combination of such properties as rigidity, surface uniformity, resistance to long term deformation, and resistance to thermal degradation.

The present invention provides a method for immobilizing biomolecules such as biopolymers, and particularly those selected from nucleic acids, proteins, polysaccharides, the method comprising the steps of:

a) providing a solid support having a surface, b) providing a reagent comprising one or more epoxide groups, and optionally also comprising one or more photogroups, c) coating the reagent on the support surface (e.g., by dipping, spraying, roll-coating or knife-coating), and covalently attaching the polymeric reagent to the support surface, e.g., by activation of the photogroups, d) providing a biopolymer (e.g., nucleic acid, protein, polysaccharide) having one or more corresponding thermochemical reactive groups (e.g., amine, hydroxyl, sulfhydryl), e) attaching the biopolymer to the support by reacting its corresponding reactive group with the bound epoxide group, f) optionally blocking the remaining unreacted epoxide groups (e.g., by the use of an amine reagent), and g) using the resultant coated support surface for its intended purpose, e.g., immobilizing biomolecules, such as nucleic acids for use in hybridization (e.g., on slides for arrays, or in microplate wells), In a preferred embodiment, the present invention provides a method of attaching a target molecule to the surface of a substrate, the method comprising:

a) providing a reagent composition comprising a polymeric backbone having one or more pendent epoxide groups adapted to form covalent bonds with corresponding functional groups on the target molecule, b) coating and immobilizing the reagent composition on the substrate surface, c) providing a solution comprising a target molecule having one or more functional groups thermochemically reactive with corresponding epoxide groups provided by the reagent composition, d) applying an amount (e.g., in the form of discrete small sample volume spots) of the solution on the surface of the substrate surface, and e) incubating the combination under conditions suitable to permit the epoxide groups provided by the reagent composition to form covalent bonds with corresponding functional groups provided by the target molecule in order to attach the target molecule to the surface.

Preferably, for use in preparing and using coated slides, the reagent is adapted to be coated and immobilized on a surface in a manner that permits:
  i) a small sample volume of a solution containing the target molecule to be applied in the form of a discrete spot on the reagent-coated surface,
  ii) target molecule present in the sample volume to become covalently attached to the bound reagent by reaction between its functional groups and the epoxide groups, and
  iii) substantially all unattached target molecule to be washed from the spot without undue detectable amounts of target molecule in the area surrounding the spot.

In a preferred embodiment, the target molecules are preferably applied to the epoxide polymer-coated surface in a solution at relatively low ionic strength and slightly alkaline pH (e.g., in 150 mM phosphate buffer, pH 8.5). Optimal coupling can be achieved by incubating the surface at high humidity (e.g., 75% relative humidity), which can be achieved by placing the surface within an enclosed storage box containing saturated NaCl at room temperature) for several hours, or most preferably, overnight. The excess uncoupled epoxide groups are then blocked with a solution containing 50 mM ethanolamine and 0.1% sodium dodecyl sulfate (SDS) in 0.1M Tris buffer, pH 9 for 30 minutes at 50° C. The surface is then rinsed with deionized water and washed with 4×standard saline citrate ("SSC")(0.6 M NaCl+ 0.06 M sodium citrate) containing 0.1% SDS at 50° C. for about 15 to about 60 minutes. The surface is then rinsed with deionized water and spun dry in a centrifuge.

When used for preparing microarrays, e.g., to attach capture probes (e.g., oligonucleotides or cDNA) to the microarray surface, such capture probes are generally delivered to the surface in a volume of less than about 1 nanoliter per spot, using printing pins adapted to form the spots into arrays having center to center spacing of about 200 μm to about 500 μm. Unlike the coupling of DNA from solution and onto the surface of coated microplate wells, nucleic acids printed in arrays of extremely small spot sizes tend to dry quickly, thereby altering the parameters affecting the manner in which the nucleic acids contact and couple with the support. In addition to the design and handling of the printing pins, other factors can also affect the spot size and/or the ultimate hybridization signals, including: salt concentrations, type of salts and wetting agents in the printing buffer; hydrophobic/hydrophilic properties of the surfaces; the size and/or concentration of the nucleic acids; and the drying environments.

In a preferred embodiment, the reagent composition can be used to prepare activated slides having the reagent composition photochemically immobilized thereon. The slides can be stably stored and used at a later date to prepare microarrays by immobilizing underivatized or amine-derivatized DNA. The coupling of the capture DNA to the surface takes place at pH 8-9 in a humid environment following printing the DNA solution in the form of small spots.

Activated slides of the present invention are particularly well suited to replace conventional (e.g., amino-silylated) glass slides in the preparation of microarrays using manufacturing and processing protocols, reagents and equipment such as micro-spotting robots (e.g., as available from Cartesian), and a micro-spotting device (e.g., as available from TeleChem International). Suitable spotting equipment and protocols are commercially available, such as the "ArrayIt"™ ChipMaker 3 spotting device. This product is said to represent an advanced version of earlier micro-spotting technology, employing 48 printing pins to deliver as many as 62,000 samples per solid substrate (e.g., 1 inch by 3 inch standard slide).

The use of such an instrument, in combination with conventional (e.g., poly-L-lysine coated) slides, is well known in the art. See, for instance, U.S. Pat. No. 5,087,522 (Brown et al.) "Methods for Fabricating Microarrays of Biological Samples", and the references cited therein, the disclosures of each of which are incorporated herein by reference.

For instance, the method and system of the present invention can be used to provide a substrate, such as a coated glass slide, with a surface having one or more microarrays. Each microarray preferably provides at least about 10/cm$^2$ (and preferably at least about 100/cm$^2$ distinct target molecules (e.g., polynucleotide or polypeptide biopolymers). Each distinct target molecule 1) is disposed at a separate, defined position in the array, 2) has a length of at least 10 subunits, 3) is present in a defined amount between about 50 attomoles and about 10 nanomoles, and 4) is deposited in selected volume in the volume range of about 0.01 nanoliters to about 100 nanoliters. These regions (e.g., discrete spots) within the array can be generally circular in shape, with a typical diameter of between about 75 microns and about 1000 microns (and preferably between about 100 and about 200 microns). The regions are also preferably separated from other regions in the array by about the same distance (e.g., center to center spacing of about 100 microns to about 1000 microns). A plurality of analyte-specific regions can be provided, such that each region includes a single, and preferably different, analyte specific reagent ("target molecule").

Those skilled in the art, given the present description, will be able to identify and select suitable reagents depending on the type of target molecule of interest. Target molecules include, but are not limited to, plasmid DNA, cosmid DNA, expressed sequence tags (ESTs), bacteriophage DNA, genomic DNA (includes, but not limited to yeast, viral, bacterial, mammalian, insect), RNA, complementary DNA (cDNA), peptide nucleic acid (PNA), and oligonucleotides.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight. Structures of the various "Compounds" identified throughout these Examples can be found in Table 1 included below.

EXAMPLE 1

Preparation of 4-Benzoylbenzoyl Chloride (BBA-Cl) (Compound I)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene:hexane to give 988 g (91% yield) after drying in a vacuum oven. Product melting point pressure and the residual thionyl chloride was removed by three evaporations using 3×500 ml of toluene. The product was recrystallized from 1:4 toluene:hexane to give 988 g (91% yield) after drying in a vacuum oven. Product melting point was 92-94° C. Nuclear magnetic resonance (NMR) analysis at 80 MHz ($^1$H NMR (CDCl$_3$)) was consistent with the desired product: aromatic protons 7.20-8.25 (m, 9H). All chemical shift values are in ppm downfield from a tetramethylsilane internal standard. The final compound was stored for use in the preparation of a monomer used in the synthesis of photoactivatable polymers as described, for instance, in Example 3.

EXAMPLE 2

Preparation of N-(3-Aminopropyl)methacrylamide Hydrochloride (APMA) (Compound II)

A solution of 1,3-diaminopropane, 1910 g (25.77 moles), in 1000 ml of CH$_2$Cl$_2$ was added to a 12 liter Morton flask and cooled on an ice bath. A solution of t-butyl phenyl carbonate, 1000 g (5.15 moles), in 250 ml of CH$_2$Cl$_2$ was then added dropwise at a rate which kept the reaction temperature below 15° C. Following the addition, the mixture was warmed to room temperature and stirred 2 hours. The reaction mixture was diluted with 900 ml of CH$_2$Cl$_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous layer was then extracted three times with 1250 ml of CH$_2$Cl$_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over Na$_2$SO$_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of CHCl$_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of CHCl$_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2 N NaOH, insuring that the aqueous layer was basic. The organic layer was then dried over Na$_2$SO$_4$ and filtered to remove drying agent. A portion of the CHCl$_3$ solvent was removed under reduced pressure until the combined weight of the product and solvent was approximately 3000 g. The desired product was then precipitated by slow addition of 11.0 liters of hexane to the stirred CHCl$_3$ solution, followed by overnight storage at 4° C. The product was isolated by filtration and the solid was rinsed twice with a solvent combination of 900 ml of hexane and 150 ml of CHCl$_3$. Thorough drying of the solid gave 900 g of N-[N'-(t-butyloxycarbonyl)-3-aminopropyl]-methacrylamide, m.p. 85.8° C. by DSC. Analysis on an NMR spectrometer was consistent with the desired product: $^1$H NMR (CDCl$_3$) amide NH's 6.30-6.80, 4.55-5.10 (m, 2H), vinyl protons 5.65, 5.20 (m, 2H), methylenes adjacent to N 2.90-3.45 (m, 4H), methyl 1.95 (m, 3H), remaining methylene 1.50-1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1$H NMR (D$_2$O) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65-2.10 (m, 2H). The final compound was stored for use in the preparation of a monomer used in the synthesis of photoactivatable polymers as described, for instance, in Example 3.

EXAMPLE 3

Preparation of N-[3-(4-Benzoylbenzamido)propyl]methacrylamide (BBA-APMA) (Compound III)

Compound II 120 g (0.672 moles), prepared according to the general method described in Example 2, was added to a dry 2 liter, three-neck round bottom flask equipped with an overhead stirrer. Phenothiazine, 23-25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1-1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene: chloroform using 23-25 mg of phenothiazine in each recrystallization to prevent polymerization. Typical yields of Compound III were 90% with a melting point of 147-151° C. Analysis on an NMR spectrometer was consistent with the desired product: $^1$H NMR (CDCl$_3$) aromatic protons 7.20-7.95 (m, 9H), amide NH 6.55 (broad t, 1H), vinyl protons 5.65, 5.25 (m, 2H), methylenes adjacent to amide N's 3.20-3.60 (m, 4H), methyl 1.95 (s, 3H), and remaining methylene 1.50-2.00 (m, 2H). The final compound was stored for use in the synthesis of photoactivatable polymers as described, for instance, in Examples 5 and 6.

EXAMPLE 4

Synthesis of a Spaced Epoxide Monomer (Compound IV)

To three ml of chloroform was added isocyanatoethylmethacrylate (1.0 ml, 7.04 mmole), glycidol (0.50 ml, 7.51 mmole) and triethylamine (50 µl, 0.27 mmole). The reaction was stirred at room temperature overnight. The product was purified on a silica gel column and the structure confirmed by NMR. The yield was 293 mg (18% yield).

EXAMPLE 5

Synthesis of a Copolymer of Acrylamide, BBA-APMA and Spaced Epoxide Monomer (Compound V)

Acrylamide (1.12 gm, 15.7 mmoles), BBA-APMA (30 mg, 0.085 mmole) and spaced epoxide monomer (Compound IV) (273 µl, 1.28 mmole) were dissolved in 15.6 ml of tetrahydrofuran (THF). To this solution was added 34 mg of 2,2'-azobisisobutyronitrile (AIBN) and 16 µl of N,N,N', N'-tetramethylethylenediamine (TEMED). The solution was sparged with helium for four minutes, then argon added to head space, then tightly capped and placed in a 55° C. oven overnight. The reaction mixture containing precipitated polymer was centrifuged and the supernatant decanted. The residue was resuspended in 20 ml of fresh THF, centrifuged and decanted. This was repeated, followed by filtering and further washing of the polymer with two ten ml aliquots of THF. The polymer was the dried under vacuum to a constant weight. The yield was 1.477 gm.

EXAMPLE 6

Preparation of Copolymer of Acrylamide, BBA-APMA, and Glycidyl Methacrylate (Photo PA-Polyepoxide) (Compound VI)

Acrylamide (7.1 gm, 99.35 mmoles), BBA-APMA (0.414 gm, 1.18 mmole) and 2,2'-azobis(2-methylbutyronitrile) ("VAZO 67", 0.262 gm, 1.4 mmole) were dissolved in 108 ml of THF. To this solution was added 2.4 ml of glycidylmethacrylate (17.7 mmoles). The solution was sparged with helium for four minutes, then with argon for four minutes, then capped tightly and heated at 61° C. overnight while mixing. The polymer was collected by filtration, then suspended in methanol and mixed, after which it was again collected by filtration and washed with chloroform, then dried in a vacuum oven at 30° C.

EXAMPLE 7

Preparation of Microscope Slides Coated with PolyEpoxide

Soda lime glass microscope slides (Erie Scientific, Portsmouth, N.H.) were silane treated by dipping in a mixture of p-tolyldimethylchlorosilane (T-Silane) and N-decyldimethylchlorosilane (D-Silane, United Chemical Technologies, Bristol, Pa.), 1% each in acetone, for 1 minute. After air drying, the slides were cured in an oven at 120° C. for one hour. The slides were then washed with acetone followed by DI water dipping. The slides were further dried in an oven for 5-10 minutes.

Compound VI was sprayed onto the silane treated slides, which were then illuminated using a Dymax lamp (25 mjoule/cm$^2$ as measured at 335 nm with a 10 nm band pass filter on an International Light radiometer) while wet, washed with water, and dried.

EXAMPLE 8

Preparation and Use of Microarrays with PhotoPA-Polyepoxide Coated Slides

PCR products derived from actin, glucose phosphate dehydrogenase (GPDH) or β-galactosidase genes were printed onto slides at 0.1 mg/ml in 0.15 M phosphate buffer using an X, Y, Z motion controller to position ChipMaker 2 microarray spotting pins (Telechem International). The slides were either coated with Photo-PA-polyepoxide as in Example 7 or polylysine slides prepared by published methods (See U.S. Pat. No. 5,087,522 (Brown et al.) "Methods for Fabricating Microarrays of Biological Samples", and the references cited therein). The printed epoxide slides were incubated overnight at room temperature and 75% relative humidity. The printed polylysine slides were UV crosslinked. After printing, the epoxide slides were blocked with 50 mM ethanolamine in 0.1M tris buffer, pH 9.0 and washed. The polylysine slides were processed by the published procedure. Both types of slides were hybridized with Cy5-labeled total RNA either spiked with β-gal mRNA at 1:250,000 or not spiked. The slides were then scanned with a laser scanner to measure intensities of Cy5 fluorescence.

| | No β-Galactosidase Spike | | | β-Galactosidase Spike | | |
|---|---|---|---|---|---|---|
| | Actin | GPDH | β-Gal | Actin | GPDH | β-Gal |
| Epoxide Coating | 33913 ± 4370 | 5984 ± 443 | 211 ± 27 | 47351 ± 2170 | 29007 ± 8825 | 9571 ± 2531 |
| Poly-L-Lysine | 29946 ± 1805 | 4751 ± 686 | 282 ± 32 | 34836 ± 2222 | 11545 ± 1882 | 4524 ± 825 |

EXAMPLE 9

Preparation and Use of Microarrays with Photo-polyepoxide Coated Slides

Oligonucleotides, either aminated or nonaminated, were printed onto slides at 8 µM in 0.15 M phosphate buffer using an X, Y, Z motion controller to position ChipMaker 2 microarray spotting pins (Telechem International). The slides were either coated with photo-PA-polyepoxide as in Example 7, with photo-PA-PolyNOS by the same procedure or with polylysine by published methods (See references in Example 8). The printed epoxide and NOS slides were incubated overnight at room termperature and 75% relative humidity. The printed polylysine slides were processed by the published procedure. The slides were scanned to measure the Cy3 fluorescence of immobilized capture oligos, then hybridized at 41° C. overnight with Cy5-labeled oligonucleotide (1 pmole/slide) that was complementary to the capture oligos. The slides were scanned with a laser scanner to measure the fluorescence intensities of the hybridized oligos. Because the amount of capture oligo immobilized with the amine-silane slides was so low, they were not hybridized.

| Coated Slides | Capture Oligo Immobilized | | Hybridization Signal | |
|---|---|---|---|---|
| | Amine-oligo | Non-amine-oligo | Amine-oligo | Non-amine-oligo |
| NOS | 30,302 ± 3866 | 5037 ± 294 | 25,226 ± 6116 | 6090 ± 503 |
| Epoxide | 36,793 ± 5145 | 30,821 ± 3585 | 26,526 ± 10887 | 28,467 ± 11695 |
| Amino-silane | 800 ± 85 | 492 ± 92 | ND | ND |

TABLE 1

Compounds

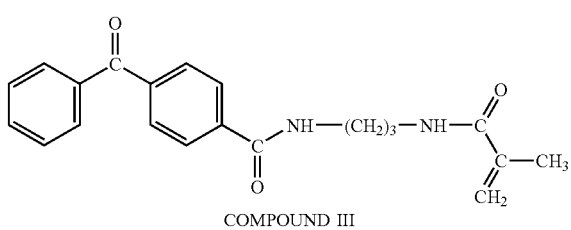

COMPOUND I

COMPOUND II

COMPOUND III

COMPOUND IV

TABLE 1-continued

Compounds

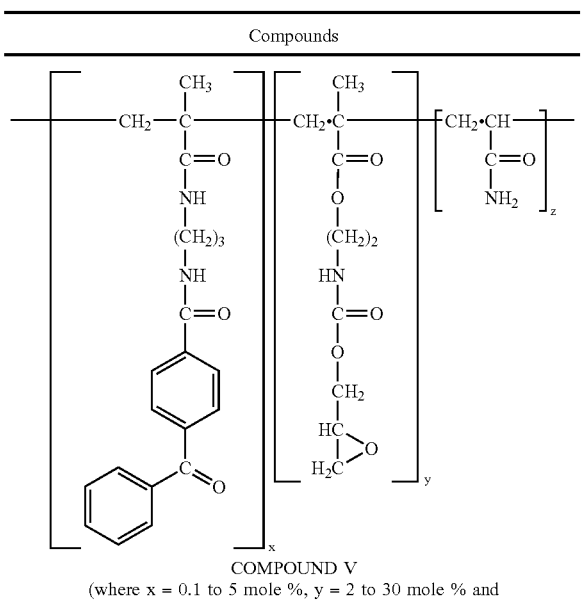

COMPOUND V
(where x = 0.1 to 5 mole %, y = 2 to 30 mole % and z = 65 to 97.9 mole %)

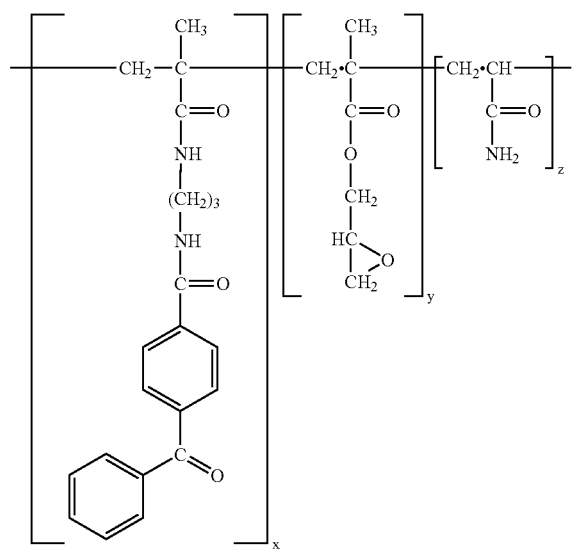

COMPOUND VI
COMPOUND VI
(where x = 0.1 to 5 mole %, y = 2 to 30 mole % and z = 65 to 97.9 mole %)

What is claimed is:

1. An activated slide comprising a flat support surface coated with a reagent composition for attaching a target molecule to the surface;

wherein the reagent composition comprises a polymeric backbone, the polymeric backbone having one or more pendent photoreactive groups and one or more pendent epoxide groups attached thereto;

wherein the reagent composition is covalently attached to the surface via activation of the pendent photoreactive groups;

and
   wherein the one or more pendent epoxide groups are capable of forming covalent bonds with the target molecules.

2. An activated slide according to claim 1 wherein the slide provides a surface for fabricating a microarray wherein the target molecule comprises a nucleic acid and the surface comprises organosilane-pretreated glass, organosilane-pretreated silicon, silicon hydride, or plastic.

3. An activated slide according to claim 1 wherein the slide provides a microarray with at least about $10/cm^2$ nucleic acids having a length of at least 10 nucleotides, the nucleic acids each being spotted in discrete regions and defined amounts of between about 50 attomoles and about 10 nanomoles.

4. An activated slide according to claim 3 wherein the regions are generally circular in shape, the regions having a diameter of between about 75 microns and about 1000 microns and separated from other regions in the microarray by center to center spacing of about 100 microns to about 1000 microns.

5. An activated slide according to claim 1 wherein the target molecule is a nucleic acid and the photoreactive group comprises photoreactive aryl ketone.

6. An activated slide according to claim 5 wherein the photoreactive aryl ketone is selected from the group consisting of acetophenone, benzophenone, anthroquinone, anthrone, and anthrone-like heterocycles.

* * * * *